(12) United States Patent
Holt et al.

(10) Patent No.: US 9,799,113 B2
(45) Date of Patent: Oct. 24, 2017

(54) MULTI-SPECTRAL THREE DIMENSIONAL IMAGING SYSTEM AND METHOD

(71) Applicant: inviCRO LLC, Boston, MA (US)

(72) Inventors: Robert W. Holt, Boston, MA (US);
Mohammed Q. Qutaish, Medford, MA (US); John W. Hoppin, Boston, MA (US); Marc E. Seaman, Norwood, MA (US); Jacob Y. Hesterman, Newton, MA (US)

(73) Assignee: inviCRO LLC, Boston, MA (US)

( * ) Notice: Subject to any disclaimer, the term of this patent is extended or adjusted under 35 U.S.C. 154(b) by 0 days.

(21) Appl. No.: 15/158,928

(22) Filed: May 19, 2016

(65) Prior Publication Data

US 2016/0343131 A1    Nov. 24, 2016

Related U.S. Application Data

(60) Provisional application No. 62/164,800, filed on May 21, 2015.

(51) Int. Cl.
*G06T 7/00* (2017.01)
*G06T 5/00* (2006.01)
*G06T 17/00* (2006.01)

(52) U.S. Cl.
CPC ............ *G06T 7/0012* (2013.01); *G06T 5/003* (2013.01); *G06T 17/00* (2013.01); *G06T 2207/10012* (2013.01); *G06T 2207/30101* (2013.01)

(58) Field of Classification Search
CPC ..... A61B 8/523; A61B 8/5238; G06T 7/0024; G06T 2207/10072; G06T 2207/10112;
(Continued)

(56) References Cited

U.S. PATENT DOCUMENTS

| 5,422,730 A | 6/1995 | Barlow et al. |
| 6,236,708 B1 * | 5/2001 | Lin ........................ A61B 6/025 378/22 |

(Continued)

FOREIGN PATENT DOCUMENTS

| CN | 101008590 | 8/2007 |
| DE | 102005042367 A1 | 3/2007 |

(Continued)

OTHER PUBLICATIONS

Zasadny et al., Pharmacokinetic and Pharmacodynamic Imaging of Intrathecally Administered Antisense Oligonucleotides, Poster session presented at: World Molecular Imaging Congress; Sep. 2-5, 2015; Honolulu, HI.

(Continued)

*Primary Examiner* — Jon Chang
(74) *Attorney, Agent, or Firm* — Hayes Soloway PC

(57) ABSTRACT

Disclosed is a computer-implemented method of creating an image of a specimen including receiving a first image of a first section of a specimen created using a first wavelength of invisible light a second image of a second section of the specimen adjacent to the first section and the second image created using the first wavelength of invisible light, co-registering the first image and the second image and creating, by the processor, a single-plane image of the first section using a next-image process.

20 Claims, 5 Drawing Sheets

(58) Field of Classification Search
CPC ...... G06T 2207/10081; G06T 2211/40; G01N 23/046; G01R 33/56
USPC .......................................................... 382/131
See application file for complete search history.

(56) References Cited

U.S. PATENT DOCUMENTS

| | | | |
|---|---|---|---|
| 6,253,653 | B1 | 7/2001 | Walter et al. |
| 6,256,366 | B1* | 7/2001 | Lai .......................... A61B 6/032 378/17 |
| 6,330,348 | B1 | 12/2001 | Kerschmann et al. |
| 6,387,653 | B1 | 5/2002 | Voneiff et al. |
| 6,631,203 | B2 | 10/2003 | Ellis et al. |
| 6,684,092 | B2 | 1/2004 | Zavislan |
| 6,800,249 | B2 | 10/2004 | de la Torre-Bueno |
| 6,992,760 | B2 | 1/2006 | Mohun et al. |
| 7,005,294 | B2 | 2/2006 | Lehmann |
| 7,372,985 | B2 | 5/2008 | So et al. |
| 7,582,872 | B2 | 9/2009 | Lewis et al. |
| 7,600,457 | B2 | 10/2009 | Voneiff et al. |
| 7,627,153 | B2 | 12/2009 | Perz et al. |
| 7,640,112 | B2 | 12/2009 | Tsipouras et al. |
| 7,677,289 | B2 | 3/2010 | Hayworth et al. |
| 7,767,414 | B1 | 8/2010 | Smith et al. |
| 7,831,075 | B2 | 11/2010 | Wilson et al. |
| 8,074,547 | B2 | 12/2011 | Ito et al. |
| 8,238,632 | B2 | 8/2012 | Wilson et al. |
| 8,366,857 | B2 | 2/2013 | Hayworth et al. |
| 8,386,015 | B2 | 2/2013 | Kamen et al. |
| 8,640,585 | B2 | 2/2014 | Zust et al. |
| 8,687,858 | B2 | 4/2014 | Walter et al. |
| 8,744,163 | B2 | 6/2014 | Morris |
| 8,771,978 | B2 | 7/2014 | Ragan |
| 8,787,651 | B2 | 7/2014 | Potts et al. |
| 8,839,700 | B2 | 9/2014 | Chen et al. |
| 8,995,733 | B2 | 3/2015 | Van Dijk et al. |
| 9,008,378 | B2 | 4/2015 | Micheva et al. |
| 9,109,982 | B2 | 8/2015 | Nakajima et al. |
| 9,117,102 | B2 | 8/2015 | Thomas et al. |
| 9,194,775 | B2 | 11/2015 | Schiffenbauer |
| 2005/0123181 | A1 | 6/2005 | Freund et al. |
| 2005/0136549 | A1 | 6/2005 | Gholap et al. |
| 2005/0235542 | A1 | 10/2005 | Metzner et al. |
| 2005/0250091 | A1 | 11/2005 | Maier et al. |
| 2006/0127880 | A1 | 6/2006 | Harris et al. |
| 2009/0263043 | A1* | 10/2009 | Cristobal Perez ...... G06T 5/003 382/275 |
| 2014/0030757 | A1 | 1/2014 | Schiffenbauer |
| 2014/0187931 | A1 | 7/2014 | Wood et al. |
| 2015/0017679 | A1 | 1/2015 | Ito |
| 2015/0078642 | A1* | 3/2015 | Fang .................. A61B 5/14553 382/131 |

FOREIGN PATENT DOCUMENTS

| | | |
|---|---|---|
| DE | 60033923 | 11/2007 |
| DE | 102009022157 B4 | 2/2010 |
| DE | 102009061014 B4 | 3/2012 |
| DE | 202013103215 U1 | 10/2013 |
| EP | 1826547 A2 | 8/2007 |
| GB | 2462360 A | 2/2010 |
| JP | H01169305 A | 7/1989 |
| JP | 2007198832 | 8/2007 |
| JP | 2010044069 | 2/2010 |
| WO | 03077749 A2 | 9/2003 |
| WO | 03105675 A2 | 12/2003 |
| WO | 2008005991 A1 | 1/2008 |

OTHER PUBLICATIONS

Holt et al., Cryofluorescence Tomography: A Versatile, High Throughput Molecular Imaging Modality, Poster session presented at: World Molecular Imaging Congress; Sep. 7-10, 2016; New York, NY.

Seaman et al., Cryofluorescence Tomography (CFT) is an ex vivo Tool to Study Anatomy, Physiology, and Drug or Tracer Distribution in Brain and Other Organs, Mol Imaging and Biol, Jul. 2016, pp. 1554-1859, vol. 18, Supplement 1, Springer, US.

Whitby et al., 10th International Symposium on the Synthesis and Applications of Isotopes and Isotopically Labelled Compounds—WBA-Drug Discovery and Development, May 11, 2010, www.interscience.wiley.com; DOI: 10.1002/Icr.1766.

Sarantopoulos et al., Imaging the Bio-Distribution of Fluorescent Probes Using Multispectral Epi-Illumination Cryoslicing Imaging, Mol Imaging Biol (2011) 13:874Y885; DOI: 10.1007/s11307-010-0416-8.

Sarder et al., Deconvolution Methods for 3-D Fluorescence Microscopy Images, IEEE Signal Processing Magazine, May 2006, pp. 32-45, vol. 23, Issue 3; DOI: 10.1109/MSP.2006.1628876.

Roy et al., 3D Cryo-Imaging: A Very High-Resolution View of the Whole Mouse, Anat Rec, 2009, pp. 342-351, vol. 292; DOI:10.1002/ar.20849.

Qutaish et al. Cryo-image Analysis of Tumor Cell Migration, Invasion, and Dispersal in a Mouse Xenograft Model of Human Glioblastoma Multiforme, Mol Imaging Biol (2012) 14: 572. DOI:10.1007/s11307-011-0525-z.

Steyer et al., Cryo-imaging of fluorescently labeled single cells in a mouse, Proc. SPIE 7262, Medical Imaging 2009: Biomedical Applications in Molecular, Structural, and Functional Imaging, 72620W (Feb. 27, 2009); DOI:10.1117/12.812982.

Steyer et al., Removal of Out-of-Plane Fluorescence for Single Cell Visualization and Quantification in Cryo-Imaging, Ann Biomed Eng (2009) 37: 1613. DOI: 10.1007/s10439-009-9726-x.

Krishnamurthi et al., Removal of subsurface fluorescence in cryo-imaging using deconvolution, Opt. Express vol. 18, Issue 21, pp. 22324-22338 (2010), DOI: 10.1364/OE.18.022324.

Gargesha et al., Visualization of color anatomy and molecular fluorescence in whole-mouse cryo-imaging, Computerized Medical Imaging and Graphics, Apr. 2011, pp. 195-205, vol. 35, Issue 3, DOI: 10.1016/j.compmedimag.2010.10.003.

Mehanna et al., Volumetric Characterization of Human Coronary Calcification by Frequency-Domain Optical Coherence Tomography, Circulation Journal, Jun. 19, 2013, pp. 2334-2340, vol. 77, Issue 9, Japanese Circulation Society, DOI: 10.1253/circj.CJ-12-1458.

Steyer et al., Detection and Quantification of Fluorescent Cell Clusters in Cryo-Imaging, International Journal of Biomedical Imaging, vol. 2012, Article ID 698413, 12 pages, 2012. DOI:10.1155/2012/698413.

Nguyen et al., Ex vivo characterization of human atherosclerotic iliac plaque components using cryo-imaging, Journal of Microscopy, Nov. 27, 2008, pp. 432-441, vol. 232, DOI: 10.1111/j.1365-2818.2008.02138.x.

Burden-Gulley et al., Novel Cryo-Imaging of the Glioma Tumor Microenvironment Reveals Migration and Dispersal Pathways in Vivid Three-Dimensional Detail, Cancer Res, Aug. 23, 2011, pp. 1-9, vol. 71, Issue 17, DOI: 10.1158/0008-5472.CAN-11-1553.

Roy et al.,, Multiscale Characterization of the PEPCK-Mouse through 3D Cryoimaging, International Journal of Biomedical Imaging, vol. 2010, Article ID 105984, 11 pages, 2010, DOI: 10.1155/2010/105984.

Holt et al., Development and Optimization of Standalone Multi-Wavelength Fluorescence Add-on for a Cryoslicer, Biomedical Optics 2016, OSA Technical Digest (online) (Optical Society of America, 2016), paper JW3A.5, DOI: 10.1364/CANCER.2016.JW3A.5.

Bernard et al., High spatial resolution measurements of organ blood flow in small laboratory animals, American Journal of Physiology—Heart and Circulatory Physiology, Nov. 1, 2000, pp. H2043-H2052, vol. 279, No. 5, American Physiological Society.

Weninger et al., A new episcopic method for rapid 3-D reconstruction: applications in anatomy and embryology, Anat Embryol, Apr. 1998, pp. 341-348, vol. 197, Issue 5, DOI: 10.1007/s004290050144.

(56) References Cited

OTHER PUBLICATIONS

Smith et al., Cryomicrotome Applications: Techniques for the Study of Skeletal Materials, Air Force Aerospace Medical Research Laboratory Aerospace Medical Division, Technical Report No. AFAMRL-TR-83-074, Sep. 1983, Govt. Accession No. AD-A137010.
Schwartz et al., Direct tissue analysis using matrix-assisted laser desorption/ionization mass spectrometry: practical aspects of sample preparation, J. Mass Spectrom., Jul. 15, 2003, pp. 699-708, vol. 38, Issue 7, DOI:10.1002/jms.505.
Faramarzalian et al., Ex Vivo Cryoimaging for Plaque Characterization, J Am Coll Cardiol Img., 2014, pp. 430-432, vol. 7, Issue 4, DOI:10.1016/j.jcmg.2013.08.017.
Roy et al., Imaging system for creating 3D block-face cryo-images of whole mice, Proc. SPIE 6143, Medical Imaging 2006: Physiology, Function, and Structure from Medical Images, 61431E, Mar. 13, 2006; DOI: 10.1117/12.655617.
Punge et al., 3D reconstruction of high-resolution STED microscope images, Microsc. Res. Tech., Sep. 2008, pp. 644-650, vol. 71, Issue 9, DOI: 10.1002/jemt.20602.
Glatz, Real-time intra-operative and endoscopic molecular fluorescence imaging, Dissertation, Dept. of Electrical Engineering and Information Technology, Oct. 27, 2014, Munich University Library of TU Munchen, http://nbn-resolving.de/urn/resolver.pl?urn:nbn:de:bvb:91-diss-20150713-1230920-1-0.

\* cited by examiner

MULTI-SPECTRAL THREE DIMENSIONAL IMAGING SYSTEM AND METHOD

CROSS REFERENCE TO RELATED APPLICATION

This application claims benefit of U.S. Provisional Application Ser. No. 62/164,800, entitled, "Multi-Spectral Three Dimensional Imaging System and Method" filed May 21, 2015, the entire disclosure of which is incorporated herein by reference.

TECHNICAL FIELD

The inventive concepts relate to imaging and more specifically to imaging using different wavelengths of light.

BACKGROUND

Multispectral fluorescence cryoslice imaging has been previously used to measure drug distribution ex-vivo in standalone or retrofitted cryoslice imagers [1,2]. Such specificity in a single imaging system can result in high cost per scan. For high throughput and low cost, it would be valuable to construct a fluorescence imager with a corresponding software package that can work in tandem with common cryoslicing instruments which are already in place. To that end, the methods outlined here demonstrate a workflow of cryofluorescence imaging techniques for a versatile, transportable add-on to existing cryoslicing instruments.

SUMMARY

Aspects of the inventive concepts include a computer-implemented method of creating an image of a specimen including: receiving, by a processor, a first image of a first section of a specimen, the first image created using a first wavelength of invisible light; receiving, by the processor, a second image of a second section of the specimen, the second section being adjacent to the first section and the second image created using the first wavelength of invisible light; co-registering, the first image and the second image; and creating, by the processor, a single-plane image of the first section using a next-image process.

Methods may include receiving, by the processor, an image of an Nth section of the specimen created using the first wavelength of invisible light; and creating, by the processor, a 3D image of the specimen using at least three images of adjacent specimen sections, which may be created using next-image processing.

Methods may further include receiving, by the processor, a third image of the first section of the specimen, the third image created using a second wavelength of invisible light; receiving, by the processor, a fourth image of a second section of the specimen, fourth image created using the second wavelength of invisible light; co-registering, by the processor the first image and the second image.

Methods may yet further include de-blurring, by the processor, the first image, determining tissue type using a visible light image and the de-blurring may be performed based on tissue type, for example, by a processor using a classification algorithm based on a stored history or library. According to aspects, the de-blurring may include one of a Monte Carlo simulation, a point spread function method and a deconvolution method. Also according to aspects, the deconvolution method may include one of a measured point spread function kernel, a simulated point spread function kernel, a Richardson-Lucy method, a Weiner filter deconvolution, a Van Cittert deconvolution, a blind deconvolution, and a regularized deconvolution method.

According to aspects, the specimen may be contacted with at least one first fluorophores having an emission spectrum in the range of approximately 200 nm to 1000 nm. And according to aspects, the specimen may be contacted with a second fluorophore, said second fluorophore having an emission spectrum in the range of approximately 200 nm to 1000 nm and different from the first fluorophore.

According to aspects, the method may further include receiving, by the processor, an image of the first section of the specimen created using visible light; and co-registering, by the processor, the images of the first section of the specimen.

According to another aspect of the inventive concepts is system for creating an image of a specimen including a light source; an image capture device; and a processor. The light source may include a visible light source and/or an invisible light source. Also according to aspects, the system may include a display and/or output means for outputting data, including an image created using the system and methods of the inventive concepts.

Another aspect includes a non-transitory program product for implementing methods of creating an image of a specimen according to the inventive concepts.

Yet another aspect of the inventive concepts includes a computer-implemented method of creating an image of a specimen, the method comprising: receiving, by a processor, an $N_X$th image of a Nth section of a specimen, the $N_X$th image created using a first wavelength of light; receiving, by the processor, an $N_Y$th image of the Nth section of the specimen, the $N_Y$th image created using a second wavelength of light, Y being equal to X+1 and M being equal to N+1, an Mth section being adjacent the Nth section; receiving, by the processor, a visible light image of the Nth section of the specimen, the visible light image created using visible light; co-registering, by the processor the $N_X$th image, the $N_Y$th image and the visible light image; and creating, by the processor, a 3D image of the specimen using a next-image process on the $N_X$th and $N_Y$th images.

The method may further include reiterating the receiving of the $N_X$th image of a Nth section of a specimen, the receiving of the $N_Y$th image of a Nth section of a specimen, the co-registering of the $N_X$th image, the $N_Y$th image and the visible image and the creating of the 3D image, where $N_X = N_X + 1$, $N_Y = N_Y + 1$ and M=M+1. The method may further include receiving a Pth light image of the Nth section when N is an integer multiple.

DETAILED DESCRIPTION

Figure 1:
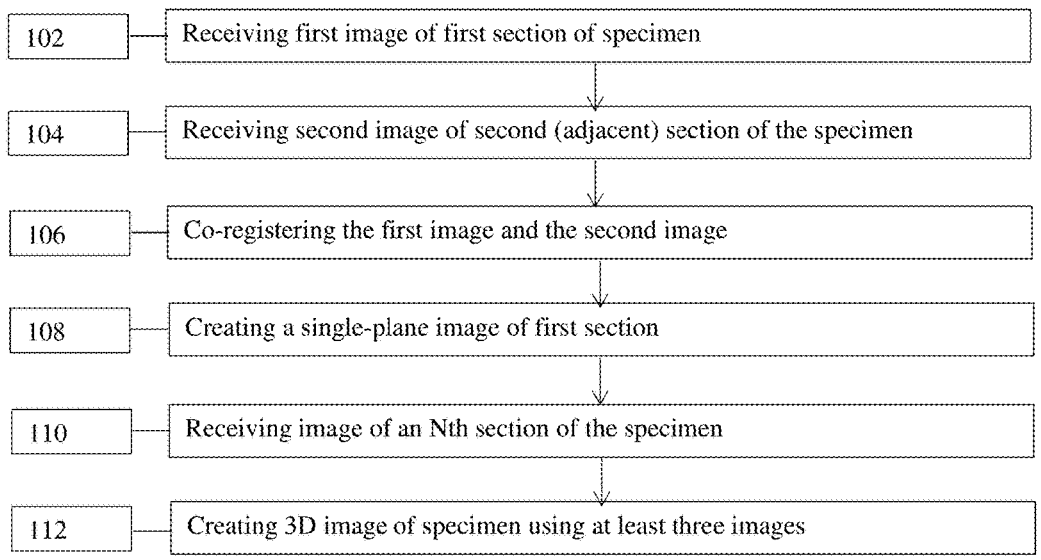
FIG. 1 is an illustrative flow chart showing processes according to inventive aspects.
Figure 1:
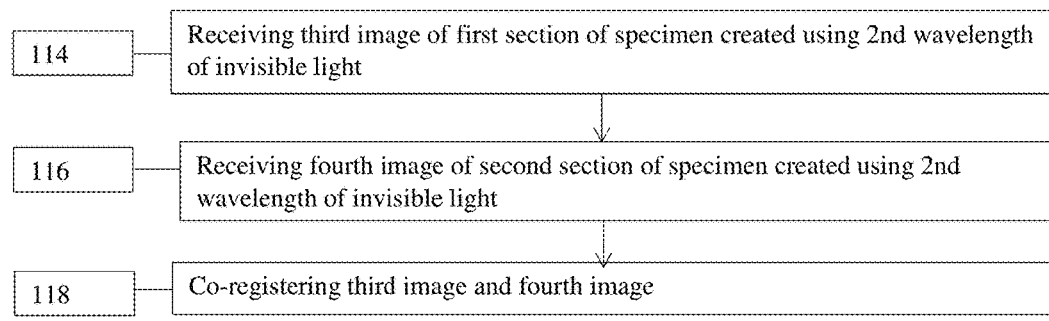

The ability to image fluorescence distribution of various substances within an animal, organ, or tissue has proven to be valuable in drug discovery and development. In vivo fluorescence imaging has proven to be a difficult problem, especially for targets at depth, due to the high scattering of optical light in tissue. In vivo bulk fluorescence imaging has been performed using tomographic recovery, as well as epi- and trans-illumination schemes. However, fluorescence recovery using these forms of imaging has been shown to have poor accuracy for deeply-seated and highly absorbing organs such as liver. Further, the resolution limit for fluorescence recovery in vivo is widely believe to be limited to a few millimeters at best, owing to the ill-posed nature of the fluorescence recovery problem. This resolution limit reduces the ability to provide any meaningful fluorescent information on relevant (e.g. vascular) characteristic length scales level beyond about a few hundred microns of depth from the surface of a subject. As drug development progresses it is less sufficient to only examine the bulk characteristics of fluorescent distribution when there is a wide field of vascular and targeted imaging agents in fluorescence. To perform fluorescence imaging with increased resolution, cryoslicing coupled with fluorescence epi-illumination imaging may be performed. While it has previously been demonstrated that drug distribution imaging can be performed with radiographic methods, fluorescence cryoslice imaging can be performed without the use of ionizing radiation. Further, many agents are shelf-stable and non-toxic. It is also possible to image several agents simultaneously using multispectral imaging techniques.

Aspects of the inventive concepts provide a simple workflow and software for a standalone (but portable) add on to a cryoslice imager, which is a common class of instrument available in many labs. However, since the fluorescence imaging system according to aspects of the inventive concepts may be constructed for transportation, it is not necessary to combine fluorescence imaging with a single cryoslicing instrument. The versatility of the instrumentation and processing schemes according to the inventive concepts lies in part in its transportability. For example, after imaging using one cryoslicing instrument designed for whole-body imaging, it may be possible to move the fluorescence instrument to another cryoslicer constructed for high-resolution, single-organ imaging.

The extension of existing cryoslice workflows to include fluorescence imaging opens the door to the use of cutting edge of molecular probes. Aspects of the invention make possible the measurement and visualization of drug distribution and/or molecular probes, administered via different delivery methods (for example, by intrathecal, oral, intravenous subcutaneous routes, by inhalation, or the like,) with molecular probes (singularly or in combination) while using the imaging schemes of the present inventive concepts. Aspects of the invention enable imaging of the area of interest, co-registration of images, and the rendering of multiple fluorophores simultaneously. Also, relative-intensity quantification may be performed, e.g., by leveraging the different properties and distributions of one or more fluorophores. Three-dimensional images can be created and displayed, which allows for detailed analysis of probe transport through regions of interest. Aspects of the inventive concepts utilize the K FLARE system, optimized for use with the commonly used fluorophores in fluorescence-guided surgery, including indocyanine green, but many other fluorophores may be imaged using methods and systems of the inventive concepts. See, for example, the probes listed in Table 1. Finally, the registration of the optical data with additional modalities such as x-ray CT and MRI may enable multi-modality validation of hybrid agents.

FIG. 1 is a flow chart showing the processes in a computer-implemented method 100 of creating an image of a specimen; the methods of which may include processes performed by a processor. A first process according to an illustrative method may include receiving, by a processor, a first image of a first section of a specimen 102, the first image created using a first wavelength of invisible light. By invisible light, it is understood that electromagnetic energy in wavelengths in the near infrared (NIR), or infrared (IR) spectrum may be included as well as electromagnetic energy such as X-Ray (as in X-ray fluorescence). In addition, ultrasound, MRI, and other modalities now known or later developed may be used for anatomical guidance. Furthermore, invisible light may include ultraviolet light. Invisible light may further include wavelengths at which any now-known or later-developed fluorophores fluoresce.

Another process in the method may include receiving a second image of a second section of the specimen 104, the second section being adjacent to the first section and the second image created using the first wavelength of invisible light. It is contemplated that serial, but non-sequential sections of the specimen may be imaged, for example, every other section, every third section, or a combination of sequential and non-sequential sections may be imaged and processed according to aspects of the inventive concepts. A next process that may be performed includes co-registering the first image and the second image 106. And a final process according to an aspect of the present inventive concepts includes creating a single-plane image of the first section 108 using a next-image process.

Optional processes that may be performed in conjunction with the above processes include receiving an image of an Nth section of the specimen 110 created using the first wavelength of invisible light. A further optional process includes creating a 3D image of the specimen using at least three images of adjacent specimen sections 112. These optional processes may be performed iteratively, N times on multiple sections to create a complete (or incomplete) 3D rendering of the specimen (or part thereof). The creation of the 3D image may be performed via next-image processing. Such a method may be described as follows, to include receiving an $N_X$th image of a Nth section of a specimen, the $N_X$th image created using a first wavelength of light; receiving an $N_Y$th image of the Nth section of the specimen, the $N_Y$th image created using a second wavelength of light, Y being equal to X+1, and M being equal to N+1, an Mth section being adjacent the Nth section; receiving a visible light image of the Nth section of the specimen, the visible light image created using visible light; co-registering, by the processor the $N_X$th image, the $N_Y$th image and the visible light image; and creating a 3D image of the specimen using a next-image process on the $N_X$th and $N_Y$th images. Methods according to the inventive concepts may include reiterating each of the following: the receiving of the $N_X$th image of a Nth section of a specimen, the receiving of the $N_Y$th image of a Nth section of a specimen, the co-registering of the $N_X$th image, the $N_Y$th image and the visible image and the creating of the 3D image, where $N_X=N_X+1$, $N_Y=N_Y+1$ and M=M+1.

Further, methods according to the present inventive concepts may include receiving a Pth light image of the Nth section where N is an integer multiple. Co-registering using light images may be useful for determining proper placement of image data and for determining tissue type. Co-registering every fluorescent image with every visible light image of the same section is likely unnecessary and each 5th, 10th, or other integer multiple (Pth) visible light image may be used for co-registration with its Pth invisible light image.

It is conceived that different fluorophores may be used such that different wavelengths of light may be imaged. Different fluorophores may be used in conjunction with specific binding to find and illuminate different proteins or structures associated with the specimen. Accordingly, a further optional process that may be performed according to inventive aspects includes receiving a third image of the first section of the specimen 114, the third image created using a second wavelength of invisible light. A next optional process may include receiving a fourth image of a second section of the specimen 116, the fourth image created using the second wavelength of invisible light. A next process may include co-registering the third image and the fourth image 118. Co-registration may be performed to ensure that same structures within different sections are properly lined up in the images.

According to aspects of the inventive concepts, the fluorophores used to contact the specimen may exhibit emission spectra in the range of approximately 200 nm to 1000 nm, and as discussed above, a plurality of fluorophores may be used on a single specimen, each fluorophore having an emission spectrum different from the others. Fluorophores can include, but are not limited to, those detailed in Table 1.

Another optional process that may be performed includes de-blurring the first image and/or any other images. De-blurring may be performed based on tissue type after tissue type is determined using a white light image. De-blurring may be performed using any appropriate method, including, but not limited to a Monte Carlo simulation, a point spread function method, and a deconvolution method. Further, the deconvolution method used may include, but is not limited to a measured point spread function kernel, a simulated point spread function kernel, a Richardson-Lucy method, a Weiner filter deconvolution, a Van Cittert deconvolution, a blind deconvolution, and a regularized deconvolution method. In another aspect of the invention, a structural image process can include a deconvolution process that probabilistically deconvolves a known point spread function from an image with a constraint that edges and regions of uniformity in the structural image are retained in the resulting fluorescence/functional image.

Another optional process includes using alternatives to white light for image recovery, de-blurring and reconstruction. Any kind of co-registered structural imaging modality (such as x-ray CT, ultrasound, MRI, etc.) may be used for an informed de-convolution.

Additionally, an image can be de-blurred first by a human or automated classification method, followed by a de-blur based on point-spread functions that are defined for each region.

The de-blurring may be performed on the first image and/or any other images. De-blurring may include a process of removing image artifacts that impair the clarity of the image. Image artifacts amenable to de-blurring can be the result of subsurface fluorescence, camera optic aberrations and other environmental effects, such as vibrations of equipment.

De-blurring may be performed based on a tissue after tissue type is determined using a white light image. De-blurring may be performed using any appropriate method, including, but not limited to a Monte Carlo simulation, a point spread function method, and a de-convolution method. Point spread functions are understood to include a means of taking a single point or combinations of multiple points in an image and correcting for image artifacts that result in a blur on the image. Point spread image functions are a preferred method for de-blurring an image where the blur is the result of subsurface fluorescence.

The de-convolution method used may include, but is not limited to, a measured point spread function kernel, a simulated point spread function kernel, a Richardson-Lucy method, a Weiner filter de-convolution, a Van Cittert de-convolution, a blind de-convolution, and a regularized de-convolution method. In another aspect of the invention, a structural image process can include a de-convolution process that probabilistically de-convolves a known point spread function from an image with a constraint that edges and regions of uniformity in the structural image are retained in the resulting fluorescence/functional image.

While the methods discussed above have mentioned imaging using invisible light as defined herein, imaging using visible light may also be used according to aspects of the inventive concepts. An optional process that may be used in conjunction with other processes, includes receiving an image of the first section of the specimen created using visible light; and co-registering the images of the first section of the specimen.

Figure 2:
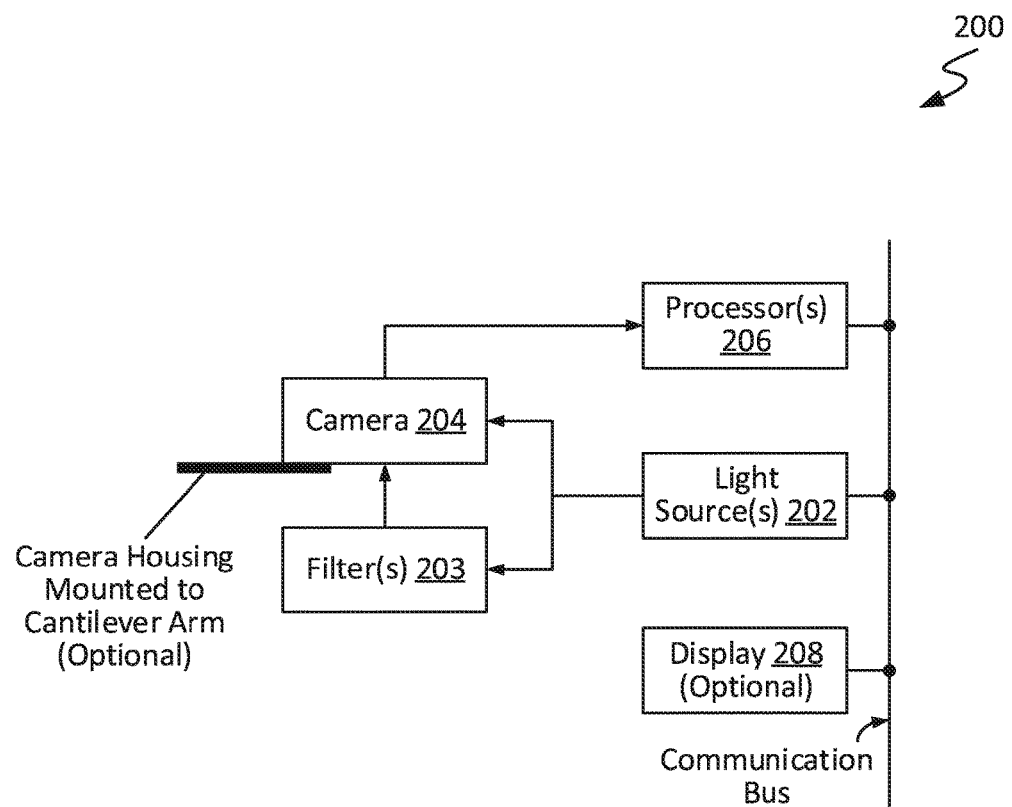
FIG. 2 illustrates devices in an environment according to inventive aspects.
Figures 3A, 3B:
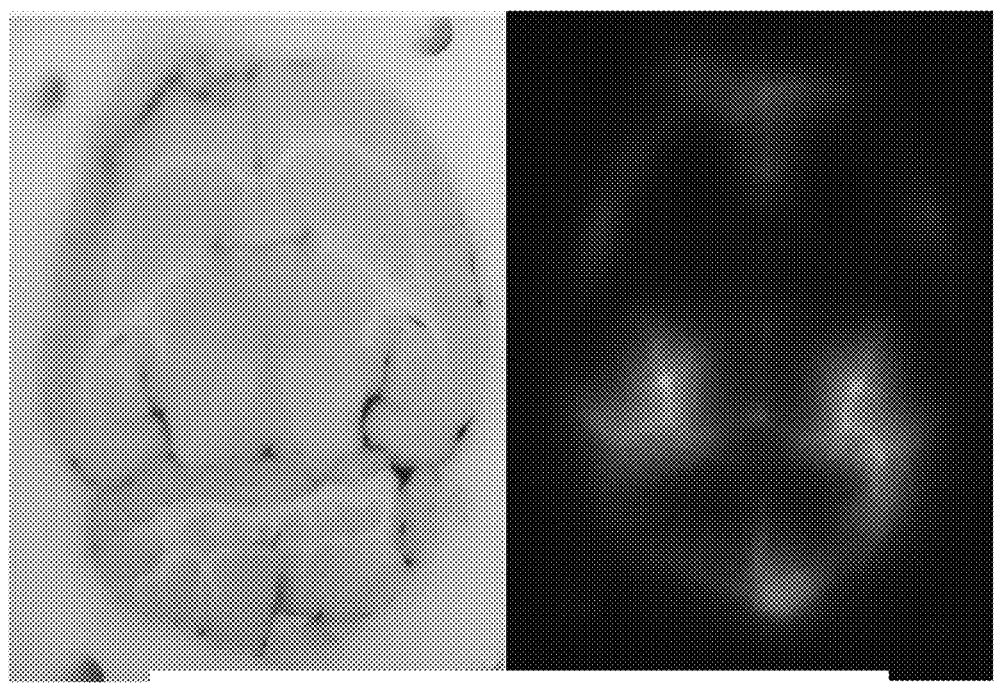
FIGS. 3A and 3B show images created using one aspect of the inventive concepts.

Also contemplated is a system for creating an image of a specimen. An illustrative system according to aspects is illustrated in FIG. 2 and includes a light source. Light source may be adapted to emit any wavelength or combination of wavelengths of light. That is, light source may emit visible light as well as wavelengths that cause fluorophores to fluoresce. Light source may be configured to emit specific wavelengths alone or simultaneously along with other wavelengths. Light source may be used in conjunction with physical filters. Also, filtering may be performed digitally, to manipulate image data to produce digitally altered images. Also illustrated is an image capture device. Image capture device may include a digital camera, a digital video capture device, a charge-coupled device (CCD), intensified charge-coupled device (iCCD), film, scintillator, optical coherence tomography, additional light and medical imaging modalities for anatomical guidance such as x-ray. System includes a processor specifically programmed to perform the methods according to the inventive concepts. Processor may be embodied in a single unit, or in multiple units either connected or not connected together. For example, a first process may be performed by a processor in one location and subsequent process may be performed by a different processor, such that the combination of the processes is performed on data that is transmitted from one processor to another. Display is illustrated. Display may be adapted to show reconstructed images created using methods according to the inventive concepts. Display may be any appropriate display, now-known, or later-developed.

According to alternative embodiments of the inventive concepts, a relatively high-resolution camera may be used which may lessen a need to co-register the images of various classes (i.e. fluorescence with the lights on versus lights off, low resolution versus high resolution white light). According to aspects, high resolution, inherently co-registered white light and fluorescence images may be simultaneously gathered and stored. Examples of high resolution that may be used according to aspects include 1024 by 1024 pixels or 36498 by 2432 pixels or any other appropriate resolution.

According to such aspects, fluorescence reconstruction may be performed as follows: White light and fluorescence images of an exposed block face are captured for each image slice. Fiducial reference markers are visible in the white light images, and are typically ink-filled holes drilled into the block. The holes are constructed to be straight, which allows the use of the holes to align one white light image with the next, (i.e., images of sequential sections may be aligned with one another). For each slice, the white light and fluorescence images are natively co-registered, meaning that when the white light images are aligned, those alignment transforms may be used to align the fluorescence images. In this manner, a fully aligned 3D distribution of white light and fluorescence information may be gathered.

In another aspect of the invention, if the fluorescence images gathered using the high-resolution camera(s) are still subject to the appearance of subsurface fluorescence, the effect of subsurface fluorescence may be removed by using a deconvolution method or a next-image processing method. The parameters required for these corrections can be determined heuristically or empirically. These parameters are likely to be different for each tissue type.

According to additional aspects of the invention, tissue identification may be performed using the white light images using color matching, atlas-registration, or hybrid techniques, without the use of additional imaging modalities such as x-ray CT or MRI or human intervention, or combinations of these. When the tissues are identified, a lookup table may be used to isolate the appropriate parameters for subsurface fluorescence removal. Each tissue may then be processed with the appropriate parameters for recovery. This results in a distribution of fluorescence as measured by corrected photon counts.

In such cases, when the system is well characterized (i.e. the efficiency and stability characteristics of all cameras and fibers is known), then this distribution can be translated into the quantitative distribution of fluorescence. Alternatively, if the total molecular count of fluorophores injected is known and the entire body has been imaged, then it is possible to use a ratiometric technique to recover the fluorescence distribution. Alternatively, if a fluorescent standard is also visible in the field of view, it will be possible to scale the fluorescence to a concentration based on the photon counts of the standard.

A workflow according to these aspects may add meta-information to the images so that the 3D fluorescence and white light images may be indexed in a database. Non-limiting examples of meta-information may include identification numbers paired with, name of subject, date of imaging, modality used to capture the information, other numbers, project- or study-specific information, pixel size or voxel size, etc. This means that the images may then be accessed through the cloud anywhere in the world.

The methods according to the inventive concepts may be embodied as a non-transitory computer program product. Any combination of one or more computer-readable storage device(s) or computer-readable media may be utilized. The computer readable medium may be a computer readable storage medium. A computer readable storage device may be, for example, but not limited to, an electronic, magnetic, optical, electromagnetic, or semiconductor system, apparatus, or device, or any suitable combination of the foregoing. More specific examples (a non-exhaustive list) of the computer readable storage device would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage device may be any tangible device or medium that can store a program for use by or in connection with an instruction execution system, apparatus, or device. The term "computer readable storage device," or variations thereof, does not encompass a signal propagation media such as a copper cable, optical fiber or wireless transmission media.

Program code embodied on a computer readable storage device or computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to one or more processors of one or more general purpose computers, special purpose computers, or other programmable data processing apparatuses to produce a machine, such that the instructions, which execute via the one or more processors of the computers or other programmable data processing apparatuses, create means for implementing the functions/acts specified in the flowchart and/or block diagram block or blocks.

These computer program instructions may also be stored in one or more computer readable storage devices or computer readable media that can direct one or more computers, one or more other programmable data processing apparatuses, or one or more other devices to function in a particular manner, such that the instructions stored in the one or more computer readable storage devices or computer readable medium produce an article of manufacture including instructions which implement the function/act specified in the flowchart and/or block diagram block or blocks.

The computer program instructions may also be loaded onto one or more computers, one or more other programmable data processing apparatuses, or one or more other devices to cause a series of operational steps to be performed on the one or more computers, one or more other programmable data processing apparatuses, or one or more other devices to produce a computer implemented process such that the instructions which execute on the one or more computers, one or more other programmable data processing apparatuses, or one or more other devices provide processes for implementing the functions/acts specified in the flowchart and/or block diagram block or blocks.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

General Method: For measurement, a subject is first prepared by the appropriate method for the study (i.e., injected with a given dose of contrast agent and then, typically sacrificed after the appropriate time.) A sample of interest is frozen in optimum cutting temperature material (O.C.T.). The O.C.T. block is serially sliced on the cryoslicer, where high-resolution white light images are taken in tandem with fluorescence images of each slice or section. Multiple fluorophores can be imaged simultaneously with the proper filtering. The section images are cropped and aligned based on anatomical and fiducial markers. If multiple cameras are used (i.e., the white light camera is located such that the subject of interest is viewed from a different angle by the white light and fluorescence camera), then a 12-parameter affine registration is performed along with the standard rigid alignment performed in cryoslice image processing. The fluorescence images are then processed using a modified form of the method presented in Steyer et al. [3], resulting in a 3D fluorescence distribution recovery which is co-registered to a white light image stack.

EXAMPLE

A naïve male Sprague-Dawley rat was injected intrathecally with 70 uL of ZW800-1 [4] at a concentration of 100 uM. The contrast agent was allowed to distribute for 90 minutes before the subject was sacrificed and the brain resected. The brain was then frozen in O.C.T. and imaged using a Leica 3050 cryostat (Leica Camera AG, Wetzlar, Germany), a high resolution Canon EOS 700 white light camera (Canon, Melville, N.Y., USA), and a K-FLARE surgical fluorescence imaging system (Curadel LLC, Worcester, Mass., USA).

Figure 4:
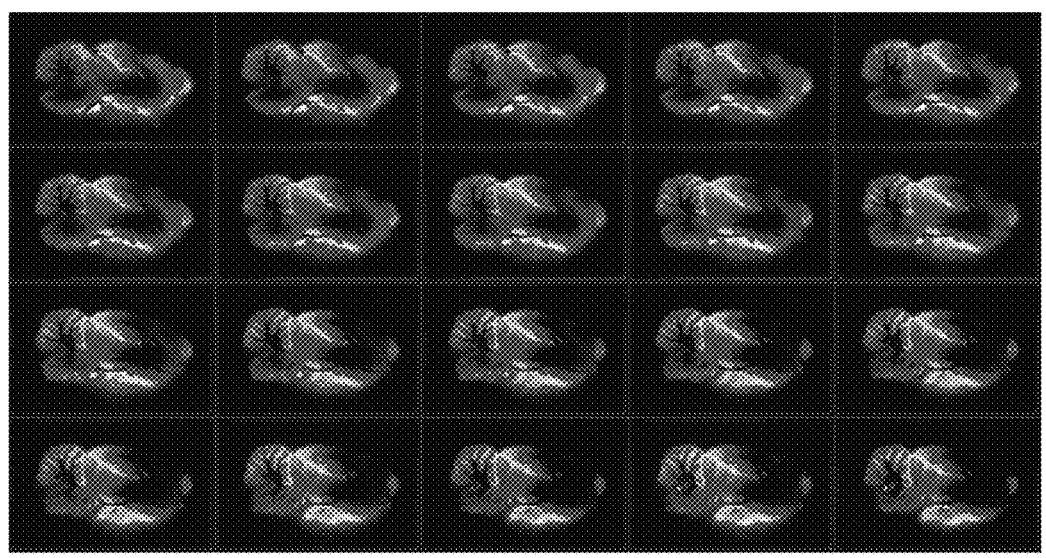
FIG. 4 is an illustrative series of serial section images captured according to inventive aspects.
Figure 5A:
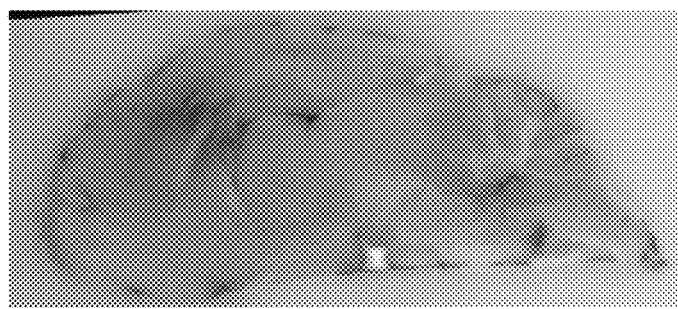
FIGS. 5A, 5B and 5C are illustrative sectional images according to aspects
Figure 5B:
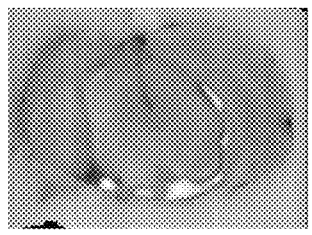
Figure 5C:
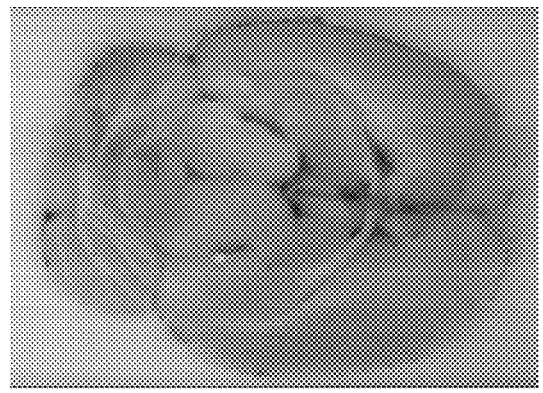

FIG. 4 shows a set of images taken on serial sections. FIGS. 5A-C show sections imaged according to aspects of the inventive concepts. Specifically, FIG. 5A shows a sagittal section, FIG. 5B illustrates a coronal section and FIG. 5C shows a transverse section of rat brain prepared and imaged according to aspects of the inventive concepts.

The measured distribution of the fluorescent tracer matches the expected distribution based on previous studies. The methodology demonstrated that versatile fluorescence imaging techniques can be performed using a standalone fluorescence imaging system in tandem with established cryoslicing instruments.

REFERENCES

[1] Roy et al., Anat Rec (2009).
[2] Sarantopoulos et al., Mol Imaging Biol (2011).
[3] Steyer et al., Annals of Biomed. Eng. (2009).
[4] Choi et al., Anger Chem Int Ed Engl (2011).

TABLE 1

List of illustrative Fluorophores

| Probe | Ex[1] (nm) | Em[2] (nm) |
|---|---|---|
| Reactive and conjugated probes | | |
| Hydroxycoumarin | 325 | 386 |
| Aminocoumarin | 350 | 455 |
| Methoxycoumarin | 360 | 410 |
| Cascade Blue | 375; 400 | 423 |
| Lucifer Yellow | 425 | 528 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| APC-Cy7 conjugates | 650; 755 | 767 |
| Red 613 | 480; 565 | 613 |
| Fluorescein | 495 | 519 |
| FluorX | 494 | 520 |
| BODIPY-FL | 503 | 512 |
| TRITC | 547 | 574 |
| X-Rhodamine | 570 | 576 |
| Lissamine Rhodamine B | 570 | 590 |
| PerCP | 490 | 675 |
| Texas Red | 589 | 615 |
| Allophycocyanin (APC) | 650 | 660 |
| TruRed | 490, 675 | 695 |
| Alexa Fluor 350 | 346 | 445 |
| Alexa Fluor 430 | 430 | 545 |
| Alexa Fluor 488 | 494 | 517 |
| Alexa Fluor 532 | 530 | 555 |
| Alexa Fluor 546 | 556 | 573 |
| Alexa Fluor 555 | 556 | 573 |
| Alexa Fluor 568 | 578 | 603 |
| Alexa Fluor 594 | 590 | 617 |
| Alexa Fluor 633 | 621 | 639 |
| Alexa Fluor 647 | 650 | 688 |
| Alexa Fluor 660 | 663 | 690 |
| Alexa Fluor 680 | 679 | 702 |
| Alexa Fluor 700 | 696 | 719 |
| Alexa Fluor 750 | 752 | 779 |
| Cy2 | 489 | 506 |
| Cy3 | (512); 550 | 570; (615) |
| Cy3, 5 | 581 | 596; (640) |
| Cy5 | (625); 650 | 670 |
| Cy5, 5 | 675 | 694 |
| Cy7 | 743 | 767 |
| Nucleic acid probes | | |
| Hoeschst 33342 | 343 | 483 |
| DAPI | 345 | 455 |
| Hoechst 33258 | 345 | 478 |
| SYTOX Blue | 431 | 480 |
| Chromomycin A3 | 445 | 575 |
| Mithramycin | 445 | 575 |
| YOYO-1 | 491 | 509 |
| SYTOX Green | 504 | 523 |
| SYTOX Orange | 547 | 570 |
| Ethidium Bromide | 493 | 620 |
| 7-AAD | 546 | 647 |
| Acridine Orange | 503 | 530/640 |
| TOTO-1, TO-PRO-1 | 509 | 533 |
| Thiazole Orange | 510 | 530 |

TABLE 1-continued

List of illustrative Fluorophores

| Probe | Ex[1] (nm) | Em[2] (nm) |
|---|---|---|
| Propidium Iodide (PI) | 536 | 617 |
| TOTO-3, TO-PRO-3 | 642 | 661 |
| LDS 751 | 543; 590 | 712; 607 |
| Fluorescent Proteins | | |
| Y66F | 360 | 508 |
| Y66H | 360 | 442 |
| EBFP | 380 | 440 |
| Wild-type | 396, 475 | 50, 503 |
| GFPuv | 385 | 508 |
| ECFP | 434 | 477 |
| Y66W | 436 | 485 |
| S65A | 471 | 504 |
| S65C | 479 | 507 |
| S65L | 484 | 510 |
| S65T | 488 | 511 |
| EGFP | 489 | 508 |
| EYFP | 514 | 527 |
| DsRed | 558 | 583 |
| Other probes | | |
| Monochlorobimane | 380 | 461 |
| Calcein | 496 | 517 |

[1]Ex: Peak excitation wavelength (nm)
[2]Em: Peak emission wavelength (nm)
See, e.g. U.S. Pat. No. 7,608,392 B2

The invention claimed is:

1. A computer-implemented method of creating an image of a specimen, the method comprising:
   receiving, by a processor, a first image of a first section of a specimen, the first image created using a first wavelength of invisible light;
   receiving, by the processor, a second image of a second section of the specimen, the second section being adjacent to the first section and the second image created using the first wavelength of invisible light;
   co-registering, by the processor, the first image and the second image;
   creating, by the processor, a single-plane image of the first section using a next-image process;
   de-blurring, by the processor, the first image; and
   determining at least one tissue type from a visible light image and wherein the de-blurring is performed based on the at least one tissue type,
   wherein the specimen is contacted with at least one first fluorophore having an emission spectrum in the range of approximately 200 nm to 1000 nm.

2. The method of claim 1, further comprising:
   receiving, by the processor, an image of an Nth section of the specimen created using the first wavelength of invisible light; and
   creating, by the processor, a 3D image of the specimen using at least three images of adjacent specimen sections.

3. The method of claim 2, wherein the creating of the 3D image is performed via a de-blurring process, wherein the de-blurring process includes one of subsurface fluorescence removal, resolving an aberration in camera optics or physical correction.

4. The method of claim 3, wherein the specimen is contacted with a first fluorophore, and a second, different fluorophore, said second fluorophore having an emission spectrum in the range of, but not limited to, approximately 200 nm to 1000 nm.

5. The method of claim 1, further comprising:
   receiving, by the processor, a third image of the first section of the specimen, the third image created using a second wavelength of invisible light;
   receiving, by the processor, a fourth image of a second section of the specimen, the fourth image created using the second wavelength of invisible light;
   co-registering, by the processor, the third image and the fourth image; and
   creating, by the processor, a single-plane image of the first section using a next-image process.

6. The method of claim 1, wherein the de-blurring includes one of an analytical solution, a Monte Carlo simulation, a point spread function method, and a deconvolution method.

7. The method of claim 6, wherein the deconvolution method includes one of: a measured point spread function kernel, a simulated point spread function kernel, a Richardson-Lucy method, a Weiner filter deconvolution, a Van Cittert deconvolution, a blind deconvolution, and a regularized deconvolution method.

8. The method of claim 1, further comprising:
   receiving, by the processor, an image of the first section of the specimen created using visible light; and
   co-registering, by the processor, the images of the first section of the specimen.

9. The method of claim 1, wherein the step of de-blurring is performed based on a plurality of tissue types.

10. A system for creating an image of a specimen comprising:
    a light source;
    an image capture device;
    a visable light source;
    a processor configured to:
       receive a first image of a first section of a specimen, the first image created using a first wavelength of invisible light;
       receive a second image of a second section of the specimen, the second section being adjacent to the first section and the second image created using the first wavelength of invisible light;
       co-register the first image and the second image; and
       create a single-plane image of the first section using a next-image process;
       receive a first visible light image of the first section of the specimen created using visible light;
       co-register the images of the first section of the specimen;
       de-blur the first image: and
       determine at least one tissue type from a visible light image, wherein the de-blurring is performed based on the at least one tissue type.

11. The system of claim 10, further comprising:
    a filter.

12. The system of claim 10, wherein the processor is further configured to:
    receive an Nth image of an Nth section of the specimen created using the first wavelength of invisible light; and
    create a 3D image of the specimen using at least three images of adjacent specimen sections.

13. The system of claim 12, wherein the creating of the 3D image is performed via a next-image process.

14. The system of claim 10, wherein the specimen is contacted with a first fluorophore and a second, different fluorophore, said second fluorophore having an emission spectrum in the range of approximately 200 nm to 1000 nm.

15. The system of claim 10, wherein the processor is further configured to:
receive a third image of the first section of the specimen, the third image created using a second wavelength of invisible light;
receive a fourth image of a second section of the specimen, the fourth image created using the second wavelength of invisible light;
co-register the third image and the fourth image; and
create a single-plane image of the first section using a next-image process.

16. The system of claim 10, wherein the de-blurring includes one of an analytical solution to optical transport, a Monte Carlo simulation, a point spread function method, and a deconvolution method.

17. The system of claim 16, wherein the deconvolution method includes one of a measured point spread function kernel, a simulated point spread function kernel, a Richardson-Lucy method, a Weiner filter deconvolution, a Van Cittert deconvolution, a blind deconvolution, and a regularized deconvolution method.

18. The system of claim 10, wherein the specimen is contacted with at least one first fluorophore having an emission spectrum in the range of approximately 200 nm to 1000 nm.

19. The system of claim 10, further comprising:
a display.

20. The system of claim 10, wherein the first image is de-blurred based on a plurality of tissue types.

* * * * *